United States Patent

Razdan et al.

[11] 4,272,540
[45] Jun. 9, 1981

[54] 14-METHOXYMORPHINAN-6-ONE COMPOUNDS AND THERAPEUTIC METHODS OF TREATING PAIN AND DRUG DEPENDENCE WITH THEM

[75] Inventors: Raj K. Razdan, Belmont; Anil C. Ghosh, Lexington, both of Mass.

[73] Assignee: SISA, Incorporated, Cambridge, Mass.

[21] Appl. No.: 32,733

[22] Filed: Apr. 24, 1979

[51] Int. Cl.³ .................. A61K 31/485; C07D 221/28
[52] U.S. Cl. .................................... 424/260; 546/74
[58] Field of Search .................. 546/74, 45; 424/260

[56] References Cited

U.S. PATENT DOCUMENTS

| | | | |
|---|---|---|---|
| 3,654,280 | 4/1972 | Sawa et al. | 546/74 |
| 3,738,989 | 6/1973 | Sawa et al. | 546/74 |
| 3,775,414 | 11/1973 | Monkovic et al. | 546/74 |
| 3,819,635 | 6/1974 | Pachter et al. | 546/74 |
| 4,100,288 | 7/1978 | Merz et al. | 424/260 |
| 4,230,712 | 11/1980 | Kotick et al. | 424/260 |
| 4,232,028 | 11/1980 | Razdan et al. | 424/260 |

OTHER PUBLICATIONS

Hirose, et al., Archives internationales de Pharmacodynamie et de Therapie, vol. 241, No. 1, pp. 79-91 (9/79).
Schneider, Nature, 220, 586-587 (1968).
Snyder, Chemical and Engineering News, 11/28/77, pp. 26, 28, 35.
Posner, "Conjugate Addition Reactions of Organocopper Reagents", Organic Reactions, vol. 19, pp. 1-114 (1972).
Monkovic, et al., Chemical Abstracts, vol. 83,193565H (1975).
Fleischhacker, et al., Chemical Abstracts, vol. 77,152408s (1972).

*Primary Examiner*—Anton H. Sutto
*Assistant Examiner*—Diana G. Rivers
*Attorney, Agent, or Firm*—Jerome L. Jeffers

[57] ABSTRACT

Disclosed are 14-methoxy substituted 3-hydroxy or 3-methoxy -6-one morphinans characterized by the structural formula:

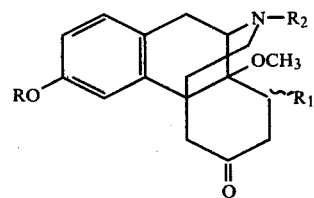

wherein R is H or methyl; $R_1$ is H, $\alpha$ methyl or $\beta$ methyl; and $R_2$ is cyclobutylmethyl, cyclopropylmethyl, tetrahydrofurfuryl or dimethylallyl. The compounds of the present invention are variously useful as analgesics, narcotic antagonists and mixed analgesics/narcotic antagonists.

46 Claims, No Drawings

14-METHOXYMORPHINAN-6-ONE COMPOUNDS AND THERAPEUTIC METHODS OF TREATING PAIN AND DRUG DEPENDENCE WITH THEM

BACKGROUND OF THE INVENTION

1. Field of the Invention

Morphine is a well known narcotic analgesic having the structural formula:

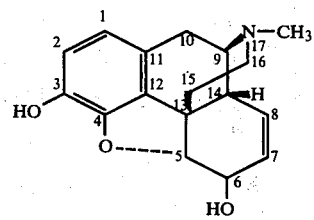

The compounds of this invention are structurally related to morphine and are named according to the morphinan system of nomenclature using the morphinan nucleus which is shown below:

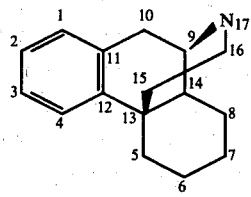

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for morphine unless otherwise indicated. In some structures, such as the general formula appearing on Page 1 hereof, a serpentine line ($\sim$) denotes orientation of a covalent bond either above or below the plane of reference.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make them less than ideal analgesics. It is impossible to predict, based on structure alone, whether a particular morphine-like compound will act as an analgesic (agonist), a narcotic antagonist or possess a combination of these properties since very minute structural modifications in the molecule result in significant changes in pharmacological activity. A compound with the appropriate profile of analgesic (agonist) and narcotic antagonist actions has potential for treatment of moderate to severe pair without the liability of drug dependence or drug abuse. Those compounds which exhibit only agonist activity are, of course, useful as analgesics whereas those compounds which exhibit only antagonist activity find utility in the treatment of drug addiction.

Prior Art

Morphinans which are hydroxy substituted in the 14-position are known. Thus, I. J. Pachter reports in *Narcotic Antagonists, Advances in Biochemical Psychopharmacology,* Vol. 8, Raven Press, New York 1973, p. 57, the preparation of compounds having the structure:

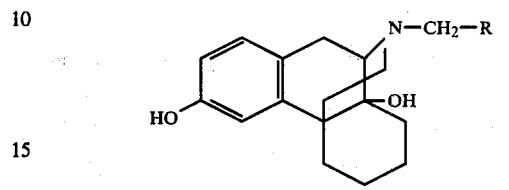

where R is cyclopropyl (A) or cyclobutyl (B). The compound in which R is cyclopropyl is reported to be essentially a narcotic antagonist while that compound in which R is cyclobutyl is reported to possess both analgesic and narcotic antagonist activity. This article also reports the preparation by the Shionogi Company in Japan of a compound having the formula:

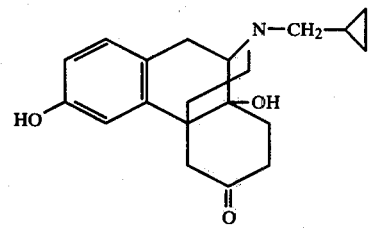

It is stated that this compound is very long acting and more potent than A (above), cyclazocine or naloxone. Naloxone is a potent narcotic antagonist whereas cyclazocine has mixed analgesic/narcotic antagonist activity.

Compounds of the general formula:

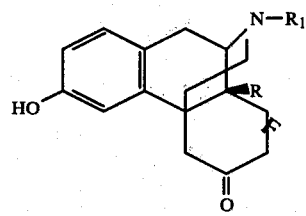

where R is a hydrogen atom or hydroxyl group; $R_1$ is allyl, $\gamma,\gamma$-dimethylallyl or cyclopropylmethyl; and F represents the presence or absence of a double bond are disclosed in U.S. Pat. No. 3,654,280 which issued Apr. 4, 1972.

SUMMARY OF THE INVENTION

The present invention involves 14-methoxy substituted-3-hydroxy or 3-methoxy-6-one morphinans characterized by the formula:

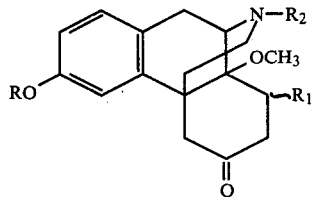

where R is H or methyl; $R_1$ is H, α methyl or β methyl; and $R_2$ is cyclobutylmethyl, cyclopropylmethyl, tetrahydrofurfuryl or dimethylallyl.

DETAILED DESCRIPTION AND PREFERRED EMBODIMENTS

The 14-methoxy substituted 3-hydroxy or 3-methoxy-6-one morphinans of the present invention are prepared as indicated by Scheme I. Referring to Scheme I, Compound 1[Sawa et al, Tetrahedron letters, 15, 154 (1961)] is treated with m-chloroperbenzoic acid in acid solution to give Compound 2 which is then reacted with methyl iodide and sodium hydride to give the 14-methoxy Compound 3. Compound 4 is obtained when 3 is hydrogenated in the presence of a catalyst such as 10% palladium on charcoal. Treatment of 4 with cyanogen bromide, followed by acid hydrolysis gives the nor Compound 6 which can be reacted with an appropriate alkyl halide to give Compounds 7, 8 and 9. The reaction is carried out according to standard laboratory procedures in a suitable inert solvent and in the presence of a base. Dimethylformamide and sodium bicarbonate have been used in the practice of this invention. Compounds 7, 8 and 9 are obtained when 6 is reacted with cyclobutylmethyl bromide, cyclopropylmethyl bromide and tetrahydrofurfuryl bromide, respectively. Boron tribromide or HBr is used to selectively dimethylate the methoxy in the 3-position while leaving the 14-methoxy unaffected, thus forming Compounds 10, 11 and 12. This reaction is carried out in an inert solvent and preferably under a dry atmosphere when boron tribromide is used as the dimethylating agent.

Scheme II shows an alternative procedure for the preparation of 4, a key intermediate in the synthesis of the compounds of this invention. Referring to Scheme II, 14-hydroxycodeinone (13) [Hauser et al, J.Med.-Chem., 17, 117 (1974)] is treated with methyl iodide and sodium hydride to give 14-methoxycodeinone (14), followed by subsequent hydrogenation to yield 15. The 4, 5-epoxy ring of 15 is opened by reacting with zinc dust and ammonium chloride in alcohol, and the resulting hydroxy in the 4-position of 16 is converted to the phenyl ether (17) by treatment with bromobenzene. The morphinone group is next protected as a ketal (18) while the phenyl ether is cleaned by treatment with sodium/-liquid ammonia. Hydrolysis of the ketal gives the desired Compound 4 which can be further reacted according to Scheme I.

SCHEME I

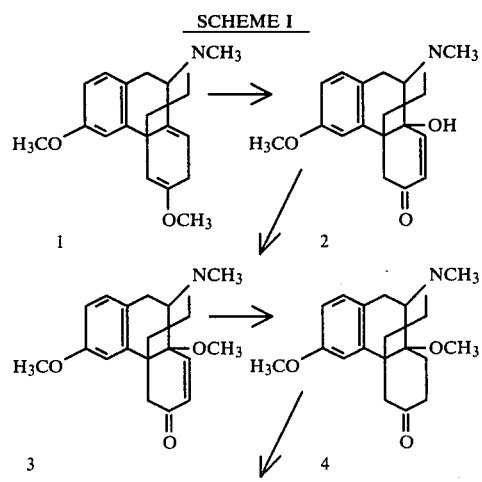

-continued

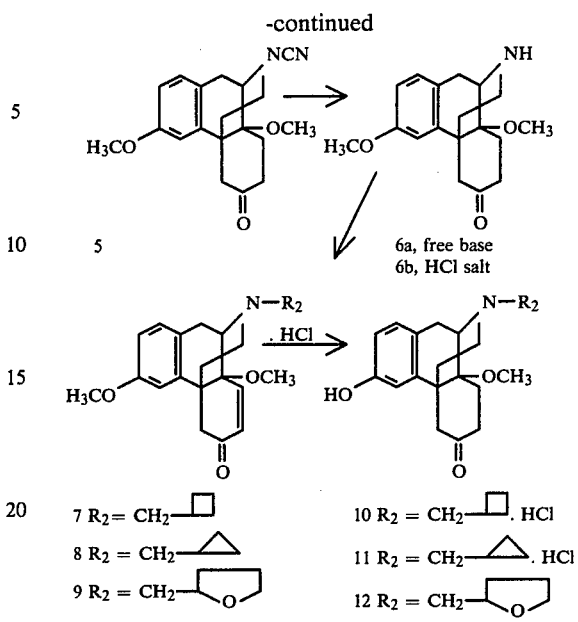

SCHEME II

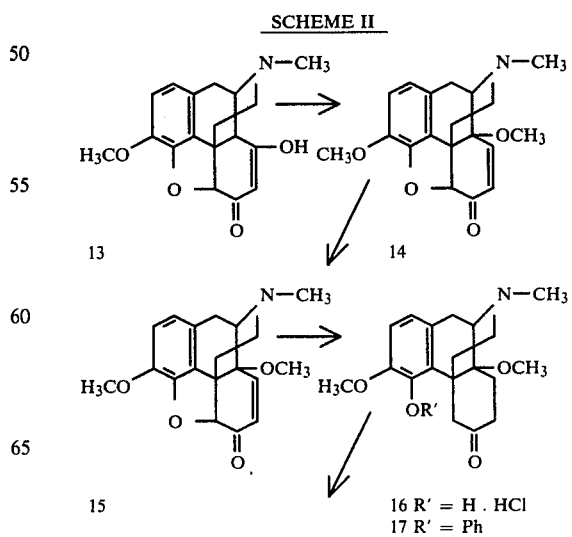

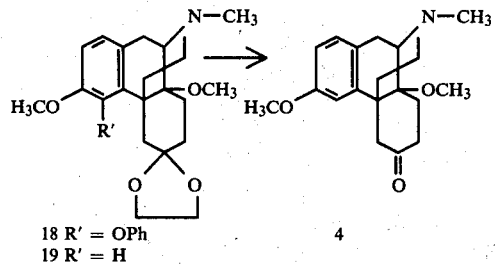

18 R' = OPh
19 R' = H

The preparation of those 14-methoxy substituted 3-hydroxy or 3-methoxy-6-one morphinans of the present invention where $R_1$ is α-methyl are prepared as set out in Scheme III. Referring to Scheme III, 14-methoxycodeinone (14) is reacted with methyl lithium and copper iodide according to the general procedure of Posner, Organic Reactions, Vol. 19, p. 1, to give the 8α-methyl substituted Compound 20. The 4, 5 epoxy ring of Compound 20 is opened by reaction with zinc dust and ammonium chloride in alcohol to give the 4-hydroxy Compound 21, which is converted to the phenoxy ether (22) by treatment with bromobenzene. The morphinone group is next protected as a ketal (23) while the phenoxy is cleaved by sodium/liquid ammonia reaction. Hydrolysis of the ketal gives Compound 24, which is treated with cyanogen bromide (25), followed by acid hydrolysis to the nor Compound 26. The nor compound was reacted according to the conditions described in Scheme I with tetrahydrofurfuryl bromide, cyclopropylmethyl bromide and cyclobutylmethyl bromide to give Compounds 29, 30 and 32, respectively. Treatment of Compounds 30 and 32 with boron tribromide selectively demethylates the methoxy at the 3-position, to give Compounds 31 and 33, without affecting the methoxy groups in the 14-position. Reaction of the morphinone group of Compound 31 with sodium borohydride gives the alcohol 34. The nor Compound 26 can also be converted to the corresponding 3-hydroxy Compound 27 and reacted with an alkyl halide as was done in the preparation of the dimethylallyl Compound 28.

The 8α substitution reaction involves treating Compound 14 with lithium dimethyl copper. This reagent and methods for its preparation are described in the above-mentioned Posner article at Pages 4 and 5. We have chosen to prepare this reagent in situ by adding methyl lithium and copper iodide to the reaction media. In copper conjugate addition reactions on morphinan-6-one-7,8-ene compounds, predominantly the β isomer is formed. We have found that when 14-methoxycodeinone 14 is reacted under these conditions, as in Example XVII hereof, the α isomer is the predominant product. This novel reaction therefore offers a method for obtaining the previously unavailable 8α substituted morphinans disclosed herein. This reaction is carried out in an inert solvent and preferably under a dry atmosphere.

SCHEME III

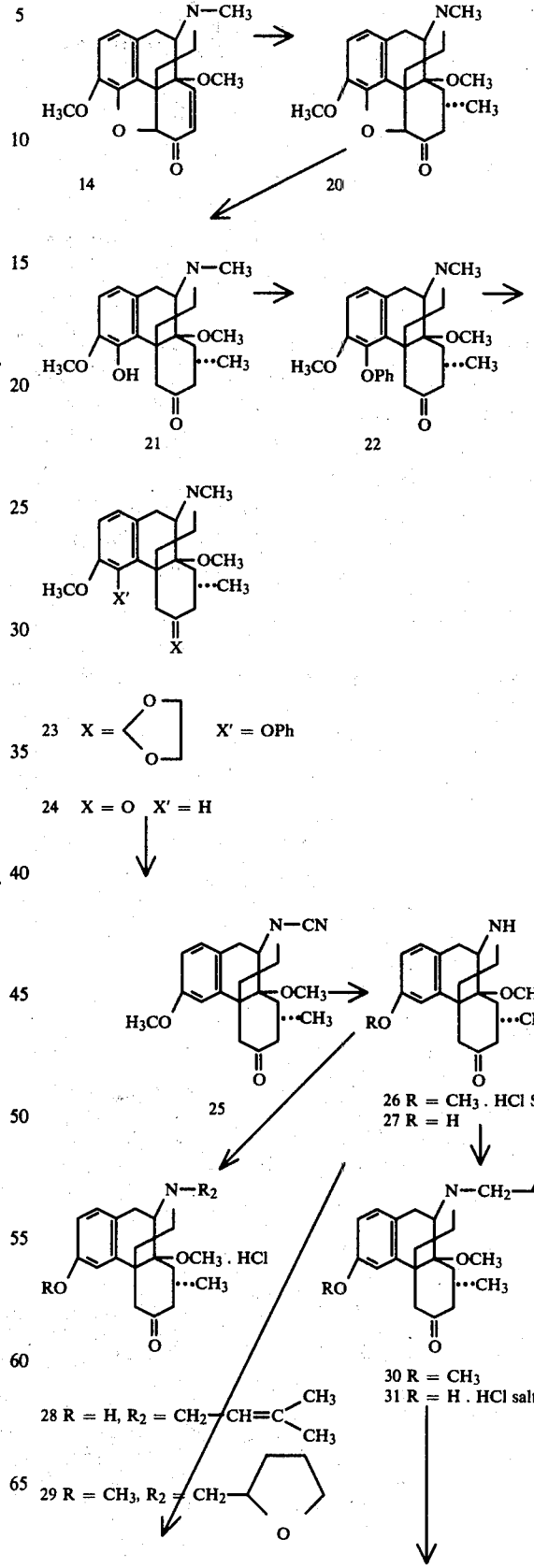

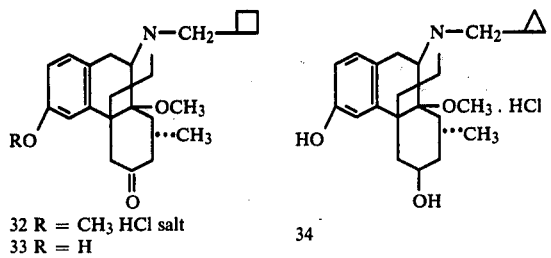

32 R = CH₃ HCl salt
33 R = H
34

The preparation of those 14-methoxy substituted 3-hydroxy or 3-methoxy-6-one morphinans of the present invention where $R_1$ is β-methyl are prepared as set out in Scheme IV. Referring to Scheme IV, Compound 3 is reacted with methyl lithium and copper iodide according to the general procedure of Posner, Organic Reactions, Vol. 19, p. 1, to give the 8β-methyl substituted Compound 35. Using a sequence of reactions similar to those described in Scheme I, the 17-methyl group of Compound 35 is converted to the nor group of Compound 37. Upon reaction with alkyl halides there are obtained Compounds 38 and 39. Compounds 40 and 41 result from the selective demethylation of the 3-methoxy groups while leaving the 14-methoxy intact. The diol Compound 42 is obtained by sodium borohydride reaction of 40.

SCHEME IV

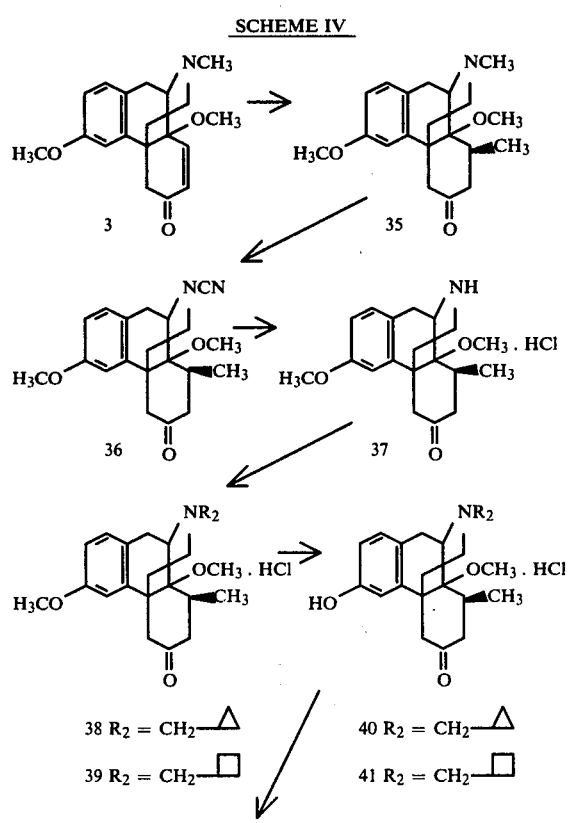

-continued
SCHEME IV

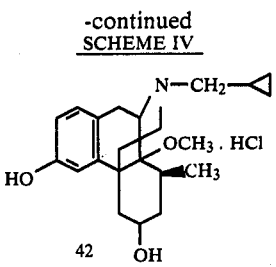

42

The preparation and pharmacology of the compounds of the present invention are more fully described in the following examples.

EXAMPLE I 7,8-Didehydro-14-hydroxy-3-methoxy-17-methylmorphinan-6-one(2)

To a stirring solution of 25 g, (0.094 mole) of 3,6-dimethoxy-17-methyl-5,6,8,14-tetrahydromorphinan (1) prepared as described by Sawa et al in Tetrahedron Letters 15, 154 (1961) in 150 ml of glacial acetic acid, 15 ml of water and trifluoroacetic acid (15.04 g, 0.132 mol) held under a nitrogen atmosphere, was added m-chloroperbenzoic acid (12 g, 0.07 mol) in small portions over a 12 minute period. The reaction flask was lowered into an oil bath preheated to 95° C. and stirred for 15 minutes whereupon the flask was removed from the bath, and while stirring, additional m-chloroperbenzoic acid (7.46 g, 0.04 mol) was added over a 15 minute period. At this point the reaction mixture was again heated in the bath for 20 minutes whereupon the flask was removed from the bath, the solution stirred for an additional 30 minutes and poured into ice water. After stirring for 30 minutes the solid was removed by suction filtration, and to the chilled filtrate was added enough ammonium hydroxide to make the solution basic and precipitate a solid. After 1 hour the solid was collected by suction filtration to give 18.3 g of crude product. Purification by chromatography on Florisil using a gradient methanol/chloroform solvent system yielded 10.0 g (36% theory) of the desired product as a colorless solid (m.p. 213°-215°).

Analysis: NMR (CDCl₃)δ2.43 (s, 3H, N—CH₃) 3.78 (s, 3H, C₃—OCH₃), 6.63-7.1 (m, 3H, aromatics). IR (neat) $v_{max}$ 1680 cm⁻¹ (>C=O).

EXAMPLE II 7,8-Didehydro-3,14-dimethoxy-17-methylmorphinan-6-one (3)

Sodium hydride (0.075 mol, 3.2 g of a 57% dispersion in mineral oil, washed under nitrogen three times with hexane to remove the oil) was suspended in 70 ml of dry tetrahydrofuran (distilled from sodium) and a solution of 2 (10.0 g, 0.0334 mol) in 450 ml of dry tetrahydrofuran was added. The mixture was stirred at room temperature for 90 minutes whereupon methyl iodide (7.02 g, 0.05 mol) was added and the reaction mixture stirred at 45°-55° for four hours and then left at ambient temperature overnight. At this point the reaction was quenched by the addition of water, the layers separated and the aqueous phase extracted four times with diethyl ether. The ether extracts were combined, washed once with water and once with saturated sodium chloride, dried over sodium sulfate and concentrated under reduced pressure. The crude orange product (7.0 g) was purified by chromatography on Florisil (graded methanol/- chloroform solvent system) to yield 5.45 g (70% theory) of the desired product.

Analysis: NMR (CDCl$_3$)δ2.43 (s, 3H, N—CH$_3$), 3.35 (s, 3H, C$_{14}$—OCH$_3$), 3.68 (s, 3H, C$_3$—OCH$_3$), 5.81 (d, 1H, C$_7$—H), 6.85 (d, 1H, C$_8$—H) and 6.47-7.07 (m, 3H, aromatics): IR (neat) $\nu_{max}$ 1680 cm$^{-1}$ (>C=O).

Anal. Calcd for C$_{19}$H$_{23}$NO$_3$·½H$_2$O: C, 71.45; H, 7.47; N, 4.39. Found: C, 71.24; H, 7.52; N, 4.27.

EXAMPLE III 3,14-Dimethoxy-17-methylmorphinan-6-one (4)

A solution of 7,8-didehydro-3,14-dimethoxy-17-methylmorphinan-6-one (3) (4.30 g, 13.72 mmol) in acetic acid (80 ml) was hydrogenated over 1.72 g of Pd/C (10%) at 3 atmospheres pressure until the hydrogen uptake was complete. The mixture was filtered through Celite and the solution concentrated under reduced pressure to give a clear oil. This oil was treated with water (100 ml) and potassium bicarbonate was added until the solution became basic. The mixture was extracted with methylene chloride (3×100 ml) whereupon the organic layer was separated, dried over MgSO$_4$ and filtered. The filtrate was concentrated under vacuum to give 4.19 g (97% theory) of the desired product as a colorless solid (m.p. 152°-156° C.).

Analysis: NMR (CDCl$_3$) δ2.42 (s, 3H, N—CH$_3$), 3.38 (s, 3H, C$_{14}$—OCH$_3$), 3.75 (s, 3H, C$_3$—OCH$_3$) and 6.60-7.10 (broad m, 3H, aromatics). IR(CHCl$_3$) $\nu_{max}$ 1710 cm$^{-1}$ (>C=O).

Anal. Calcd. for C$_{19}$H$_{25}$NO$_3$: C, 72.34; H, 8.00; N, 4.44. Found: C, 72.15; H, 7.95; N, 4.34.

EXAMPLE IV

17-Cyano-3,14-dimethoxymorphinan-6-one (5)

A solution of 3,14-dimethoxy-17-methylmorphinan-6-one (0.490 g, 1.55 mmol) in methylene chloride (25 ml) was treated with cyanogen bromide (0.977 g, 9.3 mmol) and anhydrous potassium carbonate (1.285 g, 9.3 mmol). The mixture was refluxed for 22 hours, filtered through Celite and the filtrate washed with water (3×50 ml). The organic solution was separated, dried over MgSO$_4$, filtered and concentrated under reduced pressure to give 0.463 g (92% theory) of the desired product as a yellow solid (m.p. 172°-176°). Recrystallization from ethanol gave 0.427 g (85% theory) of the product as a white solid, m.p. 176°-177° C.

Analysis: NMR (CDCl$_3$) δ3.48 (s, 3H, C$_{14}$—OCH$_3$), 3.78 (s, 3H, C$_3$—OCH$_3$), 6.65-7.13 (broad m, 3H, aromatics). IR (CHCl$_3$) δmax 2240 (N—CN), 1710 cm$^{-1}$ (>C=O).

Anal. Calcd. for C$_{19}$H$_{22}$N$_2$O$_3$: C, 69.90; H, 6.81; N, 8.58. Found: C, 69.77; H, 6.88; N, 8.60.

EXAMPLE V 3,14-Dimethoxymorphinan-6-one (6)

To 17-cyano-3,14-dimethoxymorphinan-6-one (5) (6.0 g, 18.38 mmol) was added 60 ml of 2 N hydrochloric acid. At this point the mixture was refluxed for 3½ hours whereupon an aliquot was removed and extracted with chloroform. The chloroform extract was separated, washed, concentrated and examined by IR, NMR or tlc to determine the presence of starting material 5 or the intermediate urea. The refluxing was continued until reaction was complete, whereupon the solution was filtered to remove extraneous solid material and the filtrate was washed with 20 ml of methylene chloride. The aqueous layer was made basic with 5% NaHCO$_3$ solution and extracted several times with methylene chloride (3×250 ml). The organic extracts were combined, dried over Na$_2$SO$_4$, filtered and concentrated to give 4.945 g (90% theory) of the free base (6a) as a white solid.

NMR (CDCl$_3$) δ3.37 (s, 3H, C$_{14}$—OCH$_3$), 3.75 (s, 3H, C$_3$—OCH$_3$) and 6.57-7.05 (m, 3H, aromatics). IR (CHCl$_3$) $\nu_{max}$ 1710 cm$^{-1}$ (>C=O).

3,14-Dimethoxymorphinan-6-one hydrochloride (6b) was prepared by refluxing 17-cyano-3,14-dimethoxymorphinan-6-one (5) (0.385 g, 1.18 mmol) in 25 ml of 2 N hydrochloric acid for 4 hours. The solution was concentrated under reduced pressure to give 0.360 g (91% theory) of (6b) as a white solid which was used without further purification in the preparation of the N-cyclobutyl derivative.

EXAMPLE VI

17-Cyclobutylmethyl-3,14-dimethoxymorphinan-6-one Hydrochloride (7) (TR-5296)

A mixture of 3,14-dimethoxymorphinan-6-one hydrochloride (6b) (1.0 g, 2.96 mmol), cyclobutylmethyl bromide (0.662 g, 4.44 mmol) and NaHCO$_3$ (1.492 g, 17.76 mmol) in 25 ml of dimethylformamide (DMF) was refluxed at an oil bath temperature of 110° under nitrogen for 16 hours. The mixture was filtered and the residue washed with DMF whereupon the filtrate was distilled under reduced pressure (oil bath temperature 30°-40° C.) and the residual material was taken up in methylene chloride (50 ml) and water (50 ml). The two layers were separated and the aqueous layer re-extracted with methylene chloride (2×50 ml). The organic layers were combined, washed with water (20 ml), dried over MgSO$_4$, filtered and concentrated under reduced pressure. The resulting solid was chromatographed on Florisil, and eluted with graded methanol/chloroform mixtures to give 17-cyclobutylmethyl-3,14-dimethoxymorphinan-6-one as a yellow oil. This material was converted to its HCl salt (7) by treatment with ethereal hydrogen chloride to give 0.507 g of a light-colored solid (42% theory), m.p. 230° C. (decomposed).

Analysis: NMR (CDCl$_3$) δ3.35 (s, 3H, C$_{14}$—OCH$_3$), 3.73 (s, 3H, C$_3$—OCH$_3$) and 6.55-7.03 (broad m, 3H, aromatics). IR (CHCl$_3$) $\nu_{max}$ at 1710 cm$^{-1}$ (>C=O).

Anal. Calcd. for C$_{23}$H$_{32}$NO$_3$Cl: C, 68.04; H, 7.96; N, 3.45; Cl, 8.73. Found: C, 67.92; H, 7.87; N, 3.58; Cl, 8.68.

EXAMPLE VII

17-Cyclopropylmethyl-3,14-dimethoxymorphinan-6-one (8) Free Base (TR-5400) Hydrochloride Salt (TR-5305)

A mixture of 3,14-dimethoxymorphinan-6-one (6a) (4.491 g, 14.9 mmol), cyclopropylmethyl bromide (3.017 g, 22.35 mmol) and NaHCO$_3$ (7.50 g, 89.4 mmol) in DMF (50 ml) was refluxed under nitrogen for 16 hours at 110° C. The mixture was filtered and the DMF removed by distillation under reduced pressure. The residue was taken up in methylene chloride (150 ml) and 150 ml of water. The two layers were separated and the aqueous layer re-extracted with methylene chloride (2×100 ml). The organic solutions were combined, washed with water (100 ml), dried over Na$_2$SO$_4$, filtered, and concentrated under reduced pressure. The resulting yellow solid was chromatographed on Florisil using graded methanol/chloroform as the eluant to give 17-cyclopropylmethyl-3,14-dimethoxymorphinan-6-one as a yellow oil which crystallized after drying the give 4.132 g (78% theory) of yellow solid. Recrystallization from ethanol gave 3.443 g (65%) of the title compound (8) (TR-5400) as colorless needles. A portion of 8 was converted to the hydrochloride salt (TR-5305) by treatment with ethereal hydrogen chloride to give a white solid, m.p. 215°–128° C.

Analysis: NMR (CDCl) δ3.43 (s, 3H, $C_{14}$—$OCH_3$); 3.77 (s, 3H, $C_3$—$OCH_3$) and 6.6–7.1 (broad m, 3H, aromatics). IR ($CHCl_3$) $\nu_{max}$ 1710 cm$^{-1}$ (>C=O).

Anal. Calcd. for $C_{22}H_{29}NO_3$: C, 74.31; H, 8.24; N, 3.94. Found: C, 74.37; H, 8.31; N, 3.91.

EXAMPLE VIII 3,14-Dimethoxy-17-tetrahydrofurfurylmorphinan-6-one Hydrochloride (9) (TR-5326)

A slurry of 3,14-dimethylmorphinan-6-one (6a) (0.24 g, 0.71 mmol), sodium bicarbonate (0.6 g, 7.14 mmol) and (±) tetrahydrofurfuryl bromide (0.4 g, 2.42 mmol) and dimethylformamide (15 ml) was heated at 110° C. for 16 hours with stirring under a nitrogen atmosphere. The mixture was filtered hot and the residue was washed with dimethylformamide (15 ml). The filtrate was distilled under vacuum (bath temperature 35° C.) and the resulting brownish material was treated with chloroform (50 ml) and water (20 ml). After separation, the aqueous layer was saturated with sodium chloride and extracted with ethyl acetate (3×20 ml) whereupon the organic extracts were combined, dried over $MgSO_4$ and filtered. The filtrate, upon concentration, was a brownish oily solid. This material was chromatographed twice over silica gel using graded methanol/chloroform mixtures to give 0.153 g (86% theory) of a mixture of the R and S isomers of the product. A part of this material (0.03 g) was converted into the hydrochloride salt by treatment with ethereal HCl to form the title compound as a tan-colored solid.

Analysis: NMR ($CDCl_3$) δ3.43 (s, 3H, $C_{14}$—$OCH_3$), 3.76 (s, 3H, $C_3$—$OCH_3$) and 6.40–7.13 (m, 3H, aromatics). IR ($CHCl_3$) $\nu_{max}$ 1715 cm$^{-1}$ (>C=O).

EXAMPLE IX

17-Cyclobutylmethyl-3-hydroxy-14-methoxymorphinan-6-one Hydrochloride (10) (TR-5306)

To a stirred solution of boron tribromide (1.503 g, 6.0 mmol) in chloroform (20 ml under nitrogen) was added a solution of 17-cyclobutylmethyl-3,14-dimethoxymorphinan-6-one (7) (0.370 g, 1.0 mmol) in 20 ml of chloroform over a period of 5 to 10 min. After 40 minutes, the reaction mixture was added to a mixture of ice (30 g) and ammonium hydroxide (10 ml). The resulting mixture was stirred for an additional 30 minutes at −5° C. whereupon an additional 50 ml of chloroform was added and the layers separated. The aqueous layer was re-extracted with chloroform (2×50 ml) whereupon the combined chloroform extracts were dried over $MgSO_4$, filtered and concentrated under reduced pressure to give a solid product. The product was chromatographed on Florisil and eluted with graded methanol/chloroform mixtures to give the free base as an oil. Treatment of this oil with ethereal HCl provided 140 mg (36% theory) of the desired product as an off-white solid.

Analysis: NMR ($CDCl_3$) δ3.37 (s, 3H, $C_{14}$—$OCH_3$), 5.75–6.28 (broad s, H, $C_3$—OH) and 6.52–6.97 (broad m, 3H, aromatics).

Anal. Calcd. for $C_{22}H_{30}NO_3Cl$: C, 67.41; H, 7.73; N, 3.57; Cl, 9.04. Found: C, 67.27; H, 7.54; N, 3.63; Cl, 8.98.

EXAMPLE X

17-Cyclopropylmethyl-3-hydroxy-14-methoxymorphinan-6-one Hydrochloride (11) (TR-5325)

To a stirred solution of boron tribromide (4.78 g, 19.08 mmol) in chloroform (75 ml under nitrogen) was added a solution of compound (8) (1.092 g, 3.18 mmol) in 100 ml of chloroform over a period of 2 to 3 minutes. After 30 minutes, the reaction mixture was added to ice (75 g) and ammonium hydroxide (15 ml) and the resulting mixture stirred for additional 30 minutes at 0° to 5° C. After addition of more chloroform (100 ml) the two layers were separated and the aqueous layer was re-extracted with chloroform (2×100 ml). The combined chloroform extracts were dried ($MgSO_4$), filtered and concentrated under reduced pressure to give a solid product. The product was chromatographed over Florisil and eluted with graded methanol/chloroform mixtures to give 17-cyclopropylmethyl-3-hydroxy-17-methoxymorphinan-6-one (11) as a yellow oil.

The free base was converted into the HCl salt by treatment with ethereal HCl (yield 0.495 g, 41% theory) to give a white solid, m.p. >260° C. (decomposed).

Analysis: NMR ($CDCl_3$) 3.42 (s, 3H, $C_{14}$—$OCH_3$), 6.13–6.47 (broad s, 1H, $C_3$—OH) and 6.53–6.97 (broad m, 3H, aromatics). IR ($CHCl_3$) $\nu_{max}$ 1710 cm$^{-1}$ (>C=O).

Anal. Calcd. for $C_{21}H_{27}NO_3$: C, 73.86; H, 7.99; N, 4.10. Found: C, 73.24; H, 8.02; N, 4.03.

EXAMPLE XI

3-Hydroxy-14-methoxy-17-tetrahydrofurfurylmorphinan-6-one (12) (TR-5340)

A solution of 3,14-dimethoxy-17-tetrahydrofurfurylmorphinan-6-one (9) (0.12 g, 0.31 mmol) in 10 ml of $CHCl_3$ was added to a solution of $BBr_3$ (0.65 g, 2.59 mmol) in 20 ml of chloroform under stirring. After 20 minutes, the product was treated with a mixture of ice (10 g), chloroform (10 ml) and $NH_4OH$ (10 ml). The resulting mixture was stirred at 0° C. for 30 minutes whereupon the layers were separated and the organic extract was washed with water. The aqueous layer was saturated with sodium chloride and re-extracted with ethyl acetate (3×15 ml). The organic extracts were combined, dried over $MgSO_4$, filtered and concentrated under reduced pressure to provide an oily solid. The material was purified by chromatography (twice) over silica gel using graded methanol/chloroform as the eluant to give a mixture of the R and S isomers, yield 0.028 g (24.3% theory).

Analysis: NMR ($CDCl_3$) δ3.37 (s, 3H, $C_{14}$—$OCH_3$) and 6.53–7.13 (m, 3H, aromatics).

EXAMPLE XII 7,8-Didehydro-3,14-dimethoxy-4,5-epoxy-17-methylmorphinan-6-one (14-Methoxycodeinone) (14)

To a suspension of sodium hydride (57% oil dispersion, 13.5 g, 0.319 mol) in 30 ml of dimethylformamide under nitrogen was added a solution of 14-hydroxycodeinone (13) [Hauser et al, J. Med. Chem., 17, 1117 (1974)] (25 g, 79.8 mmol) in 450 ml of DMF. The mixture was stirred at room temperature for 1 hour and cooled in an ice bath whereupon methyl iodide (15.5 g, 0.109 mol) was added dropwise and the mixture was allowed to warm up to room temperature. Stirring was continued for another 3 hours and at the end of this period the excess sodium hydride was decomposed very cautiously by the dropwise addition of water. Most of the DMF was removed by vacuum distillation (oil bath temperature 35°-40° C.) and the residue was taken up in 400 ml of methylene chloride. The organic layer was washed with water (3×100 ml), saturated sodium chloride solution (2×100 ml) and again with water (3×100 ml). The aqueous layer was re-extracted with methylene chloride (2×300 ml) and the organic extracts were combined. After drying over $MgSO_4$ and filtration, the organic solution was concentrated under reduced pressure to give an orange-brown residue (19.7 g). A solution of the residue in chloroform was passed through a column of Florisil (400 g) and eluted with graded chloroform/benzene mixtures. The fractions containing compound (14) were collected and the product was recrystallized from ethanol to give 13.6 g (50% theory) of 14-methoxycodeinone (14) as a tan solid, 143°-144° C.

Analysis: NMR ($CDCl_3$) $\delta 2.48$ (s, 3H, N—$CH_3$), 3.28 (s, 3H, $C_{14}$—$OCH_3$), 4.73 (s, 1H, $C_5$—H) and 6.43-6.80 (m. 2H, aromatics). IR ($CHCl_3$) $\nu_{max}$ 1683 cm$^{-1}$ (>C=O).

Anal. Calcd. for $C_{19}H_{21}NO_4$: C, 69.70; H, 6.47; N, 4.28. Found: C, 69.73; H, 6.46; N, 4.17.

EXAMPLE XIII 3,14-Dimethoxy-4,5-epoxy-17-methylmorphinan-6-one (15)

7,8-Didehydro-3,14-dimethoxy-4,5-epoxy-17-methylmorphinan-6-one (14) (5.0 g, 15.27 mmol) was hydrogenated in methanol (75 ml) over 500 mg Pd/charcoal (10%) at 3 atm. After filration through Celite the solvent was removed under reduced pressure to afford 4.92 g (98% theory) of a white solid 15, mp 140°-142° C. Recrystallization from ethanol gave 4.52 g (90% theory) of 15 as a white solid, mp 146°-146.5° C.

Analysis: NMR ($CDCl_3$) $\delta 2.40$ (s, 3H, N—$CH_3$), 3.33 (s, 3H, $C_{14}$—$OCH_3$), 3.88 (s, 3H, $C_3$—$OCH_3$), 4.6 (s, 1H, $C_5$—H), 6.65 (s, 2H, aromatics). IR ($CHCl_3$) $\nu_{max}$ 1720 cm$^{-1}$ (>C=O).

Anal: Calcd for $C_{19}H_{23}NO_4$: C, 69.27; H, 7.05; N, 4.25. Found: C, 69.27; H, 7.02; N, 4.21.

EXAMPLE XIV 3,14-Dimethoxy-4-hydroxy-17-methylmorphinan-6-one Hydrochloride (16)

A mixture of 15 (1.67 g), Zn dust (0.72 g), ammonium chloride (1.1 g) and ethanol (45 ml) was refluxed for 6 hour under $N_2$ atmosphere. The product was filtered and the residual solid washed with ethanol. The filtrate was concentrated under reduced pressure to give the hydrochloride salt of 16 as a white solid (2.71 g). This product contained some ammonium chloride but was used without purification in the next reaction. Attempts to purify the material by preparation of the free base resulted in loss of material.

Anal: Calcd for $C_{19}H_{25}NO_4$ (free base): C, 68.85, H, 7.60; N, 4.23. Found: C, 68.70; H, 7.52; N, 4.29.

EXAMPLE XV 3,14-Dimethoxy-17-methyl-4-phenoxymorphinan-6-one (17)

To a solution of crude 16 (16 g) in dry pyridine (200 ml) was added bromobenzene (22.5 g, 143.29 mmol) and 18 g (159.178 mmol) of $K_2CO_3$ (freshly dried at 110° C. for 2 hour in a vacuum oven and quickly ground and sieved to 200 mesh). More pyridine (20 ml) followed by copper powder (1.5 g, 10 micron) was added and the mixture was refluxed (oil bath temp 140°-150° C.) for 20 hr under a $N_2$ atmosphere with stirring. The solution was filtered hot, and the residue washed with hot pyridine. The filtrate was concentrated under reduced pressure to give crude 17 (10.5 g) as a foamy solid. The product was purified by chromatography on silia gel using graded methanol/chloroform to give 7.83 g (80% yield from 15) of 17 as a foamy solid.

EXAMPLE XVI 3,14-Dimethoxy-17-methylmorphinan-6-one (4)

A solution of the ketone 17 (7.43 g, 18.23 mmol) in ethylene glycol (30 ml) was combined with p-toluenesulfonic acid (8.5 g) in benzene (250 ml) and refluxed with stirring for 8 hours using a Dean Stark apparatus to azeotropically remove water which formed. After cooling, the benzene solution was separated, washed with 10% sodium carbonate solution and then with water. After drying ($MgSO_4$) and filtration, the benzene solution was concentrated under reduced pressure to give 8.14 g of 18 as a foamy solid (99% theory). IR ($CHCl_3$) of this material showed absence of the ketone group.

A solution of the crude ketal 18 (8 g), in dry, freshly distilled THF (250 ml) was added to distilled liquid ammonia (350 ml) with stirring. The mixture was treated with sodium (2.5 g), which was added in small pieces. Aftr the blue color persisted for 30 min., an excess of ammonium chloride was added in small portions, until the color disappeared. Wet ether, followed by few drops of water, was added next. The excess ammonia was allowed to evaporate overnight and the residual material was taken up in diethyl ether (350 ml). This was washed with sodium hydroxide solution (5%) and then with water. The organic extract was dried ($MgSO_4$), filtered and concentrated under reduced pressure to give 15.9 g of 19 (92% theory) which was dissolved in 5% HCl (150 ml). The mixture was refluxed for 1 hour and after cooling, the product made basic with dilute ammonia and extracted with benzene (3×200 ml). The organic layer was washed with water, dried ($MgSO_4$), filtered and concentrated to give 4.34 g of 4 as a solid (yield 85% from the ketal 19). A portion of the product was recrystallized from ethanol to give colorless crystals, mp 165°-166° C. NMR of this material was identical with the sample prepared by the method of Scheme I.

EXAMPLE XVII 3,14-Dimethoxy-8α,17-dimethyl-4,5-epoxymorphinan-6-one (20)

To a suspension of copper iodide (10.49 g, 57.3 mmol) in dry tetrahydrofuran (50 ml) and diethyl ether (50 ml), cooled in an ice bath, methyl lithium (60 ml of a 1.84 molar solution, 0.11 mol) was added under a nitrogen atmosphere. After 10 minutes, a solution of 14-methoxycodeinone (14) (15.0 g, 45.8 mmol) in tetrahydrofuran (300 ml) was added and the mixture was stirred for another 3 hours. At the end of this period, a saturated solution of ammonium chloride (200 ml) was added slowly. This was followed by the addition of a 20% NaOH solution until the mixture was basic. The aqueous layer was separated and extracted with ethyl acetate (3×100 ml) whereupon the organic extracts were combined, washed once with water (100 ml), dried over $MgSO_4$, filtered and evaporated to give crude (20). This material was recrystallized from ethanol to give 8 g (51% theory) of the title compound as a colorless solid, m.p. 204°–205° C.

Analysis: NMR (CDCl$_3$) δ0.52 (d, 3H, C$_{8\alpha}$—CH$_3$), 2.4 (s, 3H, N—CH$_3$), 3.4 (s, 3H, C$_{14}$—OCH$_3$), 3.97 (s, 3H, C$_3$—OCH$_3$), 4.86 (s, 1H, C$_5$—H) and 6.52–6.83 (m, 2H, aromatics). IR (CHCl$_3$) $\nu_{max}$ 1723 cm$^{-1}$ (>C=O).

Anal. Calcd. for C$_{20}$H$_{25}$NO$_4$. C, 69.95; H, 7.34; N, 4.08. Found C, 69.99; H, 7.26; N, 3.97.

EXAMPLE XVIII 3,14-Dimethoxy-8α,17-dimethyl-4-hydroxymorphinan-6-one (21)

A mixture of 3,14-dimethoxy-8α,17-dimethyl-4,5-epoxymorphinan-6-one (20) (1.15 g, 3.348 mmol), zinc dust (1.31 g, 20.04 mmol), ammonium chloride (1.1 g, 20.56 mmol) and ethanol (50 ml) was refluxed for six hours. The product was filtered, washed with ethanol, and the filterate was concentrated under reduced pressure to give 1.1 g of the hydrochloride salt of 3,14-dimethoxy-8α,17-dimethyl-4-hydroxymorphinan-6-one (21). The free base of this material was generated by taking up the hydrochloride salt in water, treatment with 10% Na$_2$CO$_3$ solution (50 ml), followed by extraction with ethyl acetate (5×100 ml). The organic extracts were combined and washed with water. The aqueous layer was separated and re-extracted with ethyl acetate (3×50 ml). At this point, the combined organic extracts were dried (MgSO$_4$), filtered and concentrated under reduced pressure to give 0.780 g (68% theory) of 3,14-dimethoxy-8α,17-dimethyl-4-hydroxymorphinan-6-one (21) as a colorless solid.

Analysis: NMR (CDCl$_3$) δ1.08 (d, 3H, C$_{8\alpha}$—CH$_3$), 2.38, (s, 3H, N—CH$_3$), 3.35 (s, 3H, C$_{14}$—OCH$_3$) and 3.83 (s, 3H, C$_3$—OCH$_3$).

Anal. Calcd. for C$_{20}$H$_{27}$NO$_4$. C, 69.54; H, 7.88; N, 4.06. Found C, 69.57; H, 7.86; N, 4.07.

EXAMPLE XIX 3,14-Dimethoxy-8α,17-dimethyl-4-phenoxymorphinan-6-one (22)

To a solution of 3,14-dimethoxy-[α,17-dimethyl-4-hydroxymorphinan-6-one (21) (0.4 g, 1.159 mmol) in dry pyridine (1 ml) was added bromobenzene (0.205 g, 1.35 mmol) and 0.216 g (1.565 mmol) of K$_2$CO$_3$ (freshly dried at 110° C. for 2 hours in a vacuum oven and quickly ground and sieved to 200 mesh). More pyridine (0.5 ml) followed by copper powder (20 mg, 10 micron) was added and the mixture was refluxed (oil bath temperature 130°–140°) for 24 hours under a nitrogen atmosphere with stirring. The mixture was filtered while hot and the residue was washed with hot pyridine (2 ml). After adding 10 ml of toluene, the solution was concentrated under reduced pressure to give (22) as a foamy solid. Thin layer chromatography on a silica gel plate (solvent system: CHCl$_3$:MeOH, 80:20) showed a single spot. The compound was quickly chromatographed on a silica gel column and eluted with graded methanol/chloroform mixtures to give 0.45 g (92% theory) of 3,14-dimethoxy-8α,17-dimethyl-4-phenoxymorphinan-6-one (22) as a foamy solid.

Analysis: NMR (CDCl$_3$) δ1.04 (d, 3H, C$_{8\alpha}$—CH$_3$), 2.38 (s, 3H, N—CH$_3$), 3.27 (s, 3H, C$_{14}$—OCH$_3$) and 3.63 (s, 3H, C$_3$—OCH$_3$). IR (CHCl$_3$) $\nu_{max}$ 1730 cm$^{-1}$ (>C=O).

EXAMPLE XX 3,14-Dimethoxy-8α,17-dimethylmorphinan -6-one (24)

Ethylene glycol (8 ml) and p-toluenesulfonic acid (2.5 g) were added to a solution of 3,14-dimethoxy-8α,17-dimethyl-4-phenoxymorphinan-6-one (22) (2.25 g, 5.33 mmol) in benzene (150 ml). The mixture was refluxed with stirring for 8 hours and the water formed was removed by azeotropic distillation. After cooling, the remaining benzene solution was washed with 10% sodium carbonate solution until basic and then washed with water until neutral. After drying (MgSO$_4$), the benzene solution was concentrated under reduced pressure to give a gum (2.33 g). Infrared analysis of the intermediate ketal (23) showed the absence of the ketone group.

A solution of the intermediate (23) in dry ether (150 ml) was added to freshly distilled liquid ammonia (90 ml) with stirring. The mixture was treated with sodium (0.35 g) which was added in small pieces. Ammonium chloride was added after the blue color presisted for about 30 minutes. At this point wet ether followed by a few drops of water was added. The excess ammonia was allowed to evaporate overnight and the residual material was taken up in diethyl ether (250 ml). This was washed with a 5% sodium hydroxide solution and then with water. The organic extracts were combined and concentrated under reduced pressure and the residue was dissolved in 20 ml of 5% HCl. After heating the mixture for 10 minutes, the product was made basic with dilute ammonia and extracted with benzene. The organic layer was washed with water until neutral, dried over MgSO$_4$, filtered and concentrated under reduced pressure to give 1.5 g (85.5% theory) of 3,14-dimethoxy-8α,17-dimethylmorphinan-6-one (24) as a colorless solid. Thin layer chromatography of this material (silica gel plates, solvent system: CHCl$_3$:MeOH, 80:20) showed a single spot.

Analysis: NMR (CDCl$_3$) δ0.77 (d, 3H, C$_{8\alpha}$—CH$_3$), 2.38 (s, 3H, N—CH$_3$), 3.4 (d, 3H, C$_{14}$—OCH$_3$) and 3.77 (s, 3H, C$_3$—OCH$_3$). IR (CHCl$_3$) $\nu_{max}$ 1710 cm$^{-1}$ (>C=O).

EXAMPLE XXI

17-Cyano-3,14-dimethoxy-8α-methylmorphinan-6-one (25)

To a solution of 3,14-dimethoxy-8α,17-dimethylmorphinan-6-one (24) (0.1 g, 0.303 mmol) in methylene chloride (3 ml) was added anhydrous potassium carbonate (0.23 g) followed by cyanogen bromide (0.2 g). The mixture was refluxed overnight under a nitrogen atmosphere with stirring. After cooling, the solution was filtered and the residue washed with excess methylene chloride. The filtrate was concentrated under reduced pressure to give 0.103 g (99% theory) of 17-cyano-3,14-dimethoxy-8α-methylmorphinan-6-one (25) as a foamy solid. Examination by thin layer chromatography showed a single spot (silica gel plates; solvent system CHCl$_3$:MeOH, 90:10). The product was used in the next reaction without purification.

EXAMPLE XXII 3,14-Dimethoxy-8α-methylmorphinan-6-one Hydrochloride (26)

A mixture of 17-cyano-3,14-dimethoxy-8α-methylmorphinan-6-one (25) (1.4 g, 4.117 mmol) and 2 N HCL (40 ml) was refluxed (oil bath temperature 120°–130°) with stirring for 4 hours. After cooling, the solution was filtered and the residue was washed with 20 milliliters of water. The filtrate was next concentrated under reduced pressure to give a syrup which was dissolved in benzene whereupon the solution was concentrated again using a Dean Stark apparatus to azeotropically remove any residual water. The concentrated material was dissolved in a small amount of ethanol, and diethyl ether was added thereto to precipitate a solid. After allowing the mixture to stand overnight at room temperature, the solid was removed by filtration and washed with dry ether to obtain 1.2 g (82% theory) of 3,14-dimethoxy-8α-methylmorphinan-6-one hydrochloride (26) as a tan solid.

EXAMPLE XXIII

3-Hydroxy-14-methoxy-8α-methylmorphinan-6-one (27)

A solution of 3,14-dimethoxy-8α-methylmorphinan-6-one hydrochloride (26) (0.25 g, 0.71 mmol) in water (20 ml) and chloroform (30 ml) was treated with an excess of 5% $Na_2CO_3$ solution until basic. The chloroform layer was separated and the aqueous layer was re-extracted with ethyl acetate (4×20 ml). The combined organic extracts were dried ($MgSO_4$), filtered and concentrated under reduced pressure to give the free base of (26) as a foam. The material was dissolved in chloroform (10 ml) and the solution was added to a solution of $BBr_3$ (0.8 g, 3.19 mmol) in chloroform (15 ml), with stirring. After 15 miutes, the reaction mixture was poured into ice (10 g) and $NH_4OH$ (10 ml) and stirred at 0° C. for 40 minutes whereupon the layers were separated and the organic layer was washed with water. The aqueous layer was saturated with sodium chloride and re-extracted with ethyl acetate (5×20 ml). The organic mixture were combined, dried ($MgSO_4$), filtered and concentrated under reduced pressure to provide 0.14 g (65% theory) of the title compound as an oily solid. Thin layer chromatography [silica gel, $CHCl_3$/MeOH (90:10)] showed a single spot. The material was used directly for conversion into the dimethylallyl derivative (28).

EXAMPLE XXIV

17-Dimethylallyl-3-hydroxy-14-methoxy-8α-methyl-morphinan-6-one Hydrochloride (28) (TR-5310)

A mixture of 3-hydroxy-14-methoxy-8α methylmorphinan-6-one (27) (0.13 g, 0.43 mmol), dimethylallyl bromide (0.125 g, 0.84 mmol) and ethanol (10 ml) was refluxed under a nitrogen atmosphere for 16 hours (oil bath temperature 105°–110° C). The mixture was filtered and the residue washed with ethanol. The filtrate upon concentration gave a solid product which was chromatographed over silica gel using graded methanol/chroloform mixtures as the eluant. Fractions containing the desired product were collected and evaporated to give total of 0.02 g (12.6% theory) of pure product. An additional 0.026 g of less pure 28 was also obtained. The pure material was converted into the HCl salt by treatment with ethereal HCl.

Analysis: NMR ($CDCl_3$) δ0.73 (d, 3H, $C_{8\alpha}$—$CH_3$), 1.72 (d, 6H, 

3.33 (s, 3H, $C_{14}$—$OCH_3$) and 6.46–7.07 (m, 3H, aromatics).

EXAMPLE XXV

17-Tetrahydrofurfuryl-3,14-dimethoxy-8α-methylmorphinan-6-one Hydrochloride (29) (TR-5327)

A mixture of 3,14-dimethoxy-8α-methylmorphinan-6-one hydrochloride (26) (0.24 g, 0.68 mmol), sodium bicarbonate (0.6 g, 7.14 mmol), (+) tetrahydrofurfuryl bromide (0.4 g, 2.42 mmol) and dimethylformamide (15 ml) was heated at 110° C. for 16 hours with stirring under a nitrogen atmosphere. The mixture was filtered hot and the residue washed with 10 milliliters of dimethylformamide. Most of the DMF was removed by distillation under high vacuum (bath temperature 35° C.) and the resulting brownish material was treated with $CHCl_3$ (50 ml) and water (25 ml). After separation of the two layers, the aqueous layer was saturated with sodium chloride and re-extracted with ethyl acetate (3×25 ml). The organic extracts were combined, dried ($MgSO_4$) and filtered. The filtrate was concentrated to an oily solid which was chromatographed over silica gel to give a mixture of R and S isomers of the product; yield 0.181 g (66.5% theory). A portion of the free base was converted to the HCl salt by treatment with ethereal HCl to form the title compound as a tan solid.

Analysis: NMR ($CDCl_3$) δ0.76 (d, 3H, $C_{8\alpha}$—$CH_3$), singlets at 3.4 and 3.43 (3H, $C_{14}$—$OCH_3$), 3.77 (s, 3H, $C_3$—$OCH_3$) and 6.53–7.17 (m, 3H, aromatics). IR ($CHCl_3$) $\nu_{max}$ 1705 $cm^{-1}$ (>C=O).

EXAMPLE XXVI

17-Cyclopropylmethyl-3,14-dimethoxy 8α-methylmorphinan-6-one (30)

A mixture of 3,14-dimethoxy-8α-methylmorphinan-6-one hydrochloride (26) (0.83 g, 2.36 mmol), cyclopropylmethyl bromide (0.51 g 3.78 mmol), anhydrous sodium carbonate (1.6 g, 15.09 mmol) and ethanol (20 ml) was refluxed at oil bath temperature of 110° C. for 18 hours with stirring under a nitrogen atmosphere. The resulting product was filtered and the residue washed with ethanol (3×35 ml). The filtrate was concentrated under reduced pressure give 0.689 g of a solid product which was purified by chromatography on silica gel using graded methanol/chloroform mixtures to provide 0.362 g (41.5% theory) of 17-cyclopropylmethyl-3,14-dimethoxy-8α-methylmorphinan-6-one (30) as a tan foamy solid.

Analysis: NMR ($CDCl_3$) δ0.77 (d, 3H, $C_{8\alpha}$—$CH_3$), 3.43 (s, 3H, $C_{14}$—$OCH_3$) and 3.76 (s, 3H, $C_3$—$OCH_3$).

EXAMPLE XXVII

17-Cyclopropylmethyl-3-hydroxy-14-methoxy 8α-methylmorphinan-6-one Hydrochloride (31) (TR-5284)

A solution of 17-cyclopropylmethyl-3,14-dimethoxy -8α-methylmorphinan-6-one (30) (0.323 g, 0.874 mmol) in chloroform (5 ml) was slowly added over a 2 to 3 minute period to a solution of boron tribromide (1.266 g, 5.053 mmol) in chloroform. A tan colored precipitate formed, and the mixture was stirred for an additional 20 minutes. The mixture was then poured carefully into a mixture of ice (8 g) and ammonium hydroxide (4 ml). After stirring the mixture at 0° to 5° C. for 40 minutes, the layers were separated and the aqueous layer was extracted with chloroform (2×20 ml). The organic extracts were combined, washed with water, dried over NaSO$_4$, filtered and concentrated under reduced pressure to give a gummy solid. The product was purified by column chromatography on silica gel using graded methanol/chloroform mixtures as eluant. Upon removal of the solvent a gum was obtained which was dissolved in a small volume of methanol whereupon dry diethyl ether was added and insoluble material was removed by filtration. To the clear solution was added a saturated solution of HCl in ether and the salt precipitated. The precipitated solid was separated by decantantion and dissolved in a small volume of methanol. Addition of dry diethyl ether to this methanolic solution gave pure 17-cyclopropylmethyl-3-hydroxy-14-methoxy-8α-methylmorphinan-6-one hydrochloride (31) as a cream colored solid (0.064 g, 19% theory).

Analysis: NMR (CDCl$_3$) δ0.77 (d, 3H, C$_{8\alpha}$—CH$_3$) and 3.41 (s, 3H, C$_{14}$—OCH$_3$).

Anal. Calcd. for C$_{22}$H$_{29}$NO$_3$.HCl.H$_2$O: C, 64.45; H, 7.80; N, 3.4. Found C, 63.65; H, 7.33; N, 3.29.

EXAMPLE XXVIII

17-Cyclobutylmethyl-3,14-dimethoxy-8α-methylmorphinan-6-one Hydrochloride (32) (TR-5219)

A mixture of 3,14-dimethoxy-8α-methylmorphinan-6-one hydrochloride (26) (0.75 g, 2.15 mmol), cyclobutylmethyl bromide (0.75 g, 5.03 mmol), anhydrous sodium carbonate (1 g, 9.43 mmol) and dimethylformamide (25 ml) was refluxed at oil bath temperature of 105° to 110° C. for 16 hours with stirring under a nitrogen atmosphere. The product was filtered hot and the residue washed with dimethylformamide whereupon the filtrate was distilled under reduced pressure (oil bath temperature 35° C.). The concentrated material was dissolved in ethyl acetate (200 ml) and washed with water (50 ml). After separation, the basic aqueous layer was re-extracted with ethyl acetate (2×100 ml) whereupon the organic extracts were combined, washed with water and dried over MgSO$_4$. The material was then filtered and concentrated to leave a solid (0.710 g) which was purified by chromatography on silica gel using graded chloroform/benzene mixtures to give 0.25 g (30.6% theory) of 17-cyclobutylmethyl-3,14-dimethoxy-8α-methylmorphinan (32) as a foamy solid. The free base was converted into the hydrochloride salt by treatment with ethereal HCl.

Analysis: NMR (CDCl$_3$) δ0.75(d, 3H, C$_{8\alpha}$—CH$_3$), 3.38 (s, 3H, C$_{14}$—OCH$_3$) and 3.76 (s, 3H, C$_3$—OCH$_3$). IR (CHCl$_3$) $\nu_{max}$ 1706 cm$^{-1}$ (>C=O).

Anal. Calcd. for C$_{24}$H$_{33}$NO$_3$.¾HCl ¼H$_2$O; C, 69.39; H, 8.3; N, 3.37.

Found: C, 69.52; H, 8.10; N, 3.75.

EXAMPLE XXIX

17-Cyclobutylmethyl-3-hydroxy-14-methoxy-8α-methylmorphinan-6-one (33) (TR-5249)

A solution of 17-cyclobutylmethyl-3,14-dimethoxy-8α-methylmorphinan-6-one (32) (0.4 g, 1.042 mmol) in chloroform (20 ml) was added to a well-stirred solution of boron tribromide (4 g, 15.97 mmol) in 50 milliliters of chloroform under a nitrogen atmosphere. After 1 hour, the product was poured into a mixture of ice (10 g) and ammonium hydroxide (10 ml) and stirring was continued for an additional hour. At this point 30 milliliters of chloroform was added and the two layers were separated. The organic extracts were washed with water and the aqueous layer was re-extracted with ethyl acetate (4×50 ml). The combined organic extracts were dried over MgSO$_4$, filtered and concentrated under reduced pressure to give the free base as an oily solid (0.331 g, 85.97% theory). The crude material was purified by chromatography on silica gel and eluted with graded methanol/benzene mixtures. The fractions containing the desired compound were combined to give 0.092 g (23.89% theory) of 17-cyclobutylmethyl-3-hydroxy-14-methoxy-8α-methylmorphinan-6-one (33) as an oil.

Analysis: NMR (CDCl$_3$) δ0.75 (d, 3H, C$_{8\alpha}$—CH$_3$) and 3.42 (s, 3H, C$_{14}$—OCH$_3$). IR (CHCl$_3$) $\nu_{max}$ 1720 cm$^{-1}$ (>C=O).

Anal. Calcd. for C$_{23}$H$_{31}$NO$_2$.⅜HCl; C, 74.31; H, 8.54; N, 3.76.

Found: C, 73.87; H, 8.53; N, 3.43.

EXAMPLE XXX

17-Cyclopropylmethyl-14-methoxy-8α-methylmorphinan-3,6-diol Hydrochloride (34) (TR-5285)

Sodium borohydride (0.38 g, 10.04 mmol) was added to a 3-necked flask fitted with a dropping funnel and a condensor. Under a nitrogen atmosphere, a solution of 20 mg of NaOH in 10 ml of methanol was added to the flask and the mixture stirred while a solution of 17-cyclopropylmethyl-3-hydroxy-14-methoxy-8α-methylmorphinan-6-one (31) (0.188 g, 0.528 mmol) in 10 ml of methanol was added dropwise. At this point the reaction mixture was stirred for four hrs. whereupon the reaction was quenched by the addition of 8 ml of 2 N HCl and heating in an oil bath for 10 minutes. The solvent was removed under reduced pressure, then 15 ml of methanol and 10 ml of water were added and the methanol removed under reduced pressure. This step was repeated whereupon the aqueous solution was made basic with solid Na$_2$CO$_3$. A white precipitate formed which was filtered off and the filtrate was extracted with chloroform (4×20 ml). The organic layer was separated, dried over Na$_2$SO$_4$ and concentrated to leave a gummy residue. The residue was chromatographed on silica gel and eluted with methanol:chloroform (50:50) containing a drop of NH$_4$OH to give the free base of (34) upon evaporation of the solvent. The free base was dissolved in chloroform and treated with ethereal HCl to give 17-cyclopropylmethyl-14-methoxy-8α-methylmorphinan-3,6-diol hydrochloride (34) as a colorless solid (0.1 g, 48% theory).

Analysis: NMR (CDCl$_3$) δ0.97 (d, 3H, C$_{8\alpha}$—CH$_3$) and 3.28 (s, 3H, C$_{14}$—OCH$_3$).

Anal. Calcd. for C$_{22}$H$_{31}$NO$_3$.¼ CHCl$_3$: C, 71.29, H, 8.31; N, 3.61. Found: C, 71.57; H, 8.45; N, 3.62.

EXAMPLE XXXI 3,14-Dimethoxy-8β,17-dimethylmorphinan-6-one (35)

A slurry of copper iodide (8.63 g, 0.045 mol) in 250 ml of anhydrous diethyl ether was cooled at −20° to −25° C. in a dry ice/carbon tetrachloride bath while being held under a nitrogen atmosphere. Methyl lithium (49.3 ml of a 1.84 M solution in ether, 0.091 mol) was cannulated into a calibrated dropping funnel and quickly added to the slurry. This complex was cooled an additional 10 minutes at −25° C. before a solution of 7,8- didehydro-3,14-dimethoxy-17-methylmorphinan-6-one (3) (9.47 g, 0.032 mol) in 60 ml of dry methylene chloride was added dropwise and washed in with an additional 30 ml of dry diethyl ether. After stirring at −20° C. for 2½ hours, the reaction mixture was quenched with 60 ml of 20% ammonium hydroxide and made basic by the addition of 50% sodium hydroxide. The resultant copper salts were removed by suction filtration and the filter cake was washed several times with diethyl ether and water. The layers were separated and the aqueous phase extracted with two additional portions of ether. The ethereal extracts were combined, washed with saturated sodium chloride solution, dried over $Na_2SO_4$ and concentrated under reduced pressure. Purification by chromatography on Flosisil (eluted with graded methanol/chloroform) yielded 4.6 g (46% theory) of the title compound.

Analysis: NMR (CDCl$_3$) δ1.02 (d, 3H, C$_{8\beta}$—CH$_3$), 2.42 (s, 3H, N—CH$_3$), 3.7 (s, 3H, C—OCH$_3$), 3.75 (s, 3H, C—OCH$_3$) and 6.6–7.07 (m, 3H, aromatics). IR (CDCl$_3$) $\nu_{max}$ 1710 cm$^{-1}$ (>C=O).

EXAMPLE XXXII

17-Cyano-3,14-dimethoxy-8β-methylmorphinan-6-one (36)

A slurry of 3,14-dimethoxy-8β,17-dimethylmorphinan-6-one (35) (4.4 g, 0.0134 mol), cyanogen bromide (4.2 g, 0.04 mol), and anhydrous potassium carbonate (5.5 g, 0.04 mol) in 140 ml of methylene chlordie was heated at reflux temperature for 22 hours under a nitrogen atmosphere. The potassium carbonate was removed by suction filtration and the filter cake washed throughly with methylene chloride. The solvent was removed from the filtrate under reduced pressure to leave 4.1 g (90% theory) of the title compound which was used in the next reaction step without further purification.

Analysis: NMR (CDCl$_3$) δ1.08 (d, 3H, C$_{8\beta}$—CH$_3$) 3.72 (s, 6H, C$_3$&C$_{14}$—OCH$_3$) and 6.63–7.13 (m, 3H, aromatics).

EXAMPLE XXXIII 3,14-Dimethoxy-8β-methylmorphinan-6-one Hydrochloride (37)

A solution of 17-cyano-3,14-dimethoxy-8β-methyl morphinan-6-one (36) (3.6 g, 0.011 mol) in 100 ml of 4 N HCl was heated at 80°–90° C. in an oil bath for 16 hours. The reaction mixture was cooled, diluted with 150 ml of H$_2$O and made basic with Na$_2$CO$_3$. The aqueous solution was extracted with four portions of chloroform, dried over Na$_2$SO$_4$ and concentrated under reduced pressure to give 3.8 g of crude product. The NMR spectrum of this crude material indicated the presence of the intermediate urea, and the crude material was therefore dissolved in 150 ml of 4 N HCl and heated at reflux for 10 additional hours. Similar workup as described above yielded 0.4 g of crude product which was taken up in diethyl ether, and treated with ethanol to give a precipitate. Collection of the precipitate by suction filtration gave 1.38 g (36% theory) of the title compound as a tan solid which was used in the next step without further purification.

Analysis: NMR (CDCl$_3$—D$_2$O) δ1.17 (d, 3H, C$_{8\beta}$—CH$_3$), 3.77 (s, 3H, C—OCH$_3$), 3.8 (s, 3H, C—OCH$_3$) and 6.67–7.13 (m, 3H, aromatics). IR (nujol) $\nu_{max}$ 1720$^{-1}$ (>C=O).

EXAMPLE XXXIV

17-Cyclopropylmethyl-3,14-dimethoxy-8β-methylmorphinan-6-one Hydrochloride (38) (TR-5209)

A slurry was made by the addition of sodium bicarbonate (1.24 g, 14.8 mol) to a solution of 3,14-dimethoxy-8β-methylmorphinan-6-one hydrochloride (37) (1.3 g, 3.7 mmol) and cyclopropylmethyl bromide (1 ml, 10.7 mmol) in 25 ml of dimethylformamide. This reaction mixture was heated at 100° C. under a nitrogen atmosphere, and after 16 hours the reaction mixture was cooled, sodium bicarbonate was removed by suction filtration and the filter cake washed thoroughly with dimethylformamide. After removal of the solvent by vacuum distallation (oil bath temperature 40°–45° C.), the residue was partitioned between ethyl acetate and water. The layers were separated and the aqueous phase was extracted with two additional portions of ethyl acetate. The organic fractions were combined, dried over Na$_2$SO$_4$ and concentrated under reduced pressure. Purification of the crude product by chromatography on Florisil (eluted with graded methanol/chloroform) yielded 1.0 g (75% theory) of the title compound as a golden oil. The hydrochloride salt of this compound was formed by taking up a sample of the oil in diethyl ether and adding ethereal hydrogen chloride to provide a colorless solid.

Analysis: NMR (free base) (CDCl$_3$) δ0.07–1.28 (m, 5H,—◁), 1.0 (d, 3H, C$_{8\beta}$—CH$_3$), 3.78 (s, 3H, C—OCH$_3$), 3.73 (s, 3H, C—OCH$_3$) and 6.52–7.02 (m, 3H, aromatics). IR (neat) $\nu_{max}$ 1710$^{-1}$ (>C=O).

Anal. Calcd. for C$_{23}$H$_{31}$NO$_3$.0.25H$_2$O: C, 73.86; H, 8.49; N, 3.75. Found: C, 73.79; H, 8.49; N, 3.71.

EXAMPLE XXXV

17-Cyclobutylmethyl-3,14-dimethoxy-8β-methylmorphinan-6-one Hydrochloride (39) (TR-5211)

A slurry was made by the addition of anhydrous NaHCO$_3$ (285 mg, 3.4 mmol) to a solution of 3,14-dimethoxy-8β-methylmorphinan-6-one hydrochloride (37) (300 mg, 0.85 mmol) and cyclobutylmethylbromide (0.27 ml, 2.6 mmol) in 10 ml of dimethylformamide. This reaction mixture was heated at 100° C. under a nitrogen atmosphere for 16 hours. The reaction mixture was then cooled, NaHCO$_3$ was removed by suction filtration and the filter cake was washed thoroughly with dimethyformamide. After removal of the solvent by vacuum distillation (oil bath temperature 40°–45° C.), the residue was partitioned between ethyl acetate and water, the layers separated and the aqueous phase extracted with two additional portions of ethyl acetate. The organic fractions were combined, dried over Na$_2$SO$_4$, and concentrated under reduced pressure. Purification of the crude product by chromatography on Florisil (eluted with graded methanol/chloroform) yeilded 201 mg (56% theory) of product. The hydrochloride salt of this material was formed by taking up a portion in diethyl ether/chloroform and adding hydrogen chloride to precipitate the salt which was isolated as a tan foam.

Analysis: NMR (free base) (CDCl$_3$) δ1.03 (d, 3H, C$_{8\beta}$—CH$_3$), 3.75 (s, 6H, C$_3$&$_{14}$—OCH$_3$) and 6.55–7.08 (m, 3H, aromatics). IR (neat) $\nu_{max}$ 1710 cm$^{-1}$ (>C=O).

EXAMPLE XXXVI

17-Cyclopropylmethyl-3-hydroxy-14-methoxy-8β-methylmorphinan-6-one Hydrochloride (40) (TR-5210)

A solution of 17-cyclopropylmethyl-3,14-dimethoxy-8β-methylmorphinan-6-one (38) (760 mg, 2.1 mmol) in 10 ml of chloroform was added to a well-stirred solution of boron tribromide (1.2 ml, 12.3 mmol) in 50 ml of chloroform under a nitrogen atmosphere at a rate slow enough to maintain the pot temperature at 25° C. After the addition was complete, the reaction mixture was stirred at room temperature for 15 minutes whereupon it was poured into a mixture of ice and ammonium hydroxide and stirred for 30 minutes at 0°–5° C. The layers were separated and the aqueous phase was extracted with two portions of chloroform. The organic fractions were combined, dried over $Na_2SO_4$ and concentrated under reduced pressure to yield 704 mg (94% theory) of product as a white foam. The hydrochloride salt of this material was formed by taking up a sample of the foam in chloroform/ethanol and adding ethereal hydrogen chloride to precipitate a white solid, m.p. >220° (decomposed).

Analysis: NMR (free base) ($CDCl_3$) δ0.07–1.28 (m, 5H, ⊲), 1.03 (d, 3H, $C_{8\beta}$—$CH_3$), 3.8 (s, 3H, $C_{14}$—$OCH_3$), 6.02 (broad s, 1H, $C_3$—OH exchangeable) and 6.5–7 (m, 3H, aromatics). IR (neat) $\nu_{max}$ 1710 cm$^{-1}$ (>C=O).

Anal. Calcd. for $C_{22}H_{29}NO_3 \cdot 0.34$ $CHCl_3$: C, 67.74; H, 7.47; N, 3.54. Found: C, 67.67; H, 7.81; N, 3.49.

EXAMPLE XXXVII

17-Cyclobutylmethyl-3-hydroxy-14-methoxy-8β-methylmorphinan-6-one Hydrochloride (41) (TR-5212)

A solution of 17-cyclobutylmethyl-3,14-dimethoxy-8β-methylmorphinan-6-one (39) (142 mg, 0.37 mmol) in 2.5 ml of chloroform was added to a well-stirred solution of boron tribromide (0.21 ml, 2.22 mmol) in 10 ml of chloroform under a nitrogen atmosphere at a rate slow enough to maintain a pot temperature of 25° C. After the addition was complete, the reaction mixture was stirred at room temperature for 20 minutes whereupon it was poured into a mixture of ice and ammonium hydroxide and stirred for an additional 40 minutes at 0° to 5° C. The layers were separated and the aqueous phase was extracted with two portions of chloroform. The organic fractions were combined, dried over $Na_2SO_4$ and concentrated under reduced pressure. The crude product was passed through a pipette Florisil column (eluted with methanol/chloroform) to remove colored impurities and subsequently 86 mg (57% theory) of product was recovered as an oil. The hydrochloride salt was formed by adding ethereal hydrogen chloride to an ethanol/chloroform solution of this material to precipitate the salt as a buff solid, m.p. 215° (decomposed).

Analysis: NMR ($CDCl_3$) δ1.0 (d, 3H, $C_{8\beta}$—$CH_3$), 3.75 (s, 3H, $C_{14}$—$OCH_3$) and 6.52–6.92 (m, 3H, aromatics). IR (neat) $\nu_{max}$ 1710 cm$^{-1}$ (>C=O).

Anal. Calcd. for $C_{23}H_{32}NO_3Cl \cdot 1.25$ $H_2O \cdot 0.075$ $CHCl_3$: C, 63.36; H, 7.97; N, 3.20; Cl, 9.93. Found: C, 63.28; H, 8.00; N, 2.93; Cl, 10.02.

EXAMPLE XXXVIII

17-Cyclopropylmethyl-14-methoxy-8β-methylmorphinan-3,6-diol Hydrochloride (42) (TR-5250)

To a stirring slurry of $NaBH_4$ (193 mg, 5.1 mmol) in 10 ml of methanol under a nitrogen atmosphere was added, from a pressure equalized dropping funnel, a solution of 17-cyclopropylmethyl-3-hydroxy-14-methoxy-8β-methylmorphinan-6-one (40) (100 mg, 0.28 mmol) in 10 milliliters of methanol. This reaction mixture was stirred at ambient temperature for four hours whereupon the reaction was quenched by the addition of 4 milliliters of 2 N HCl and then heated at reflux temperature in an oil bath for 10 minutes. The solvent was removed under reduced pressure and the residue taken up in 15 ml of methanol and 10 ml of water whereupon the methanol was removed under vacuum and the procedure repeated. The aqueous solution was made basic by the addition of $Na_2CO_3$, extracted with 4 portions of chloroform, dried over $Na_2SO_4$ and concentrated under reduced pressure to provide 95 mg (86% theory) of product. The hydrochloride salt of this material was formed by taking up a portion in $CHCl_3$ and adding hydrogen chloride to precipitate a buff solid, m.p. >220° (decomposed).

Analysis: NMR (free base) ($CDCl_3$) δ1.0 (d, 3H, $C_{8\beta}$—CH), 3.62 (s, 3H, $C_{14}$—$OCH_3$), 6.5–7.05 (m, 3H, aromatics). IR (solution $CHCl_3$) $\nu_{max}$ ~3200 cm$^{-1}$ (—OH).

Anal. Calcd. for $C_{22}H_{32}NO_3Cl \cdot 2.4$ $H_2O \cdot 0.15$ $CHCl_3$: C, 58.45; H, 8.19; N, 3.08; Cl, 11.29. Found: C, 58.68; H, 7.89; N, 2.71; Cl, 11.46.

PHARMACOLOGICAL EVALUATION

The compounds whose preparation is disclosed in the foregoing examples were screened to determine the following biological activities:

(A) Analgesic effects upon mice (acetic acid writhing test).

(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. J. R. Whittle, Brit. J. Pharmacol., 22:296 (1964). In this test at least three groups of five male CD-1 mice each were given subcutaneous doses of the test drug dissolved in either distilled water or distilled water acidified with HCl depending on the solubility of the compound. In all cases, 0.4 milliliter of a 0.5% V/V acetic acid in distilled water solution was administered intraperitoneally 15 minutes post drug. The number of writhes in a 20 minute interval beginning 5 minutes after the acetic acid injection were determined and compared with the number of writes in control groups which had received only acetic acid.

Percent inhibition of writhing was calculated as:

$$\% \text{ inhibition} = \frac{\text{No. control writhes} - \text{No. treated writhes}}{\text{No. control writhes}}$$

The $ED_{50}$ dose, i.e., the dose required to reduce the number of writhes by 50%, was determined graphically from a plot of % inhibition as a probit versus log dose.

Confidence limits of 95% were calculated on the basis of those results falling in the range 16–84% inhibition. See Litchfield, J. T. and Wilcoxon, F., J. Pharmacol. Exp. Ther., 96, 99–113, (1949).

TEST B. EVALUATION OF NARCOTIC ANTAGONIST ACTIVITY

The narcotic antagonist effects of test compounds were determined by a modification of the rat tail flick procedure of Harris and Pierson (J. Pharmacol. Exp. Ther. 143:141[1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds. Animals with a control reaction time outside this range are rejected. The rheostat adjustment is made only if a significant proportion (more than 2 out of every 10 rats) of the reaction times are outside the range of two to four seconds. Groups of five rats were used each time, and two control times were determined at 60 and 30 minutes prior to subcutaneous injection of the drug. A ten second cutoff time is employed; if the rat does not flick its tail in 10 seconds it is removed from the heat source.

Thirty minutes after the last control run the test drug was given interperitoneally. This was followed ten minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \frac{MRT^* \text{ (Treated)} - MRT \text{ (Control} \times 100)}{10 - MRT \text{ (Control)}}$$

$$\% \text{ Antagonism } = \frac{E \text{ (morphine controls)} - E \text{ (drug treated)} \times 100}{E \text{ (morphine control)}}$$

*MRT is defined as mean reaction time.

The data were plotted on log-probit paper and $AD_{50}$ values, i.e., the dose required to inhibit the morphine effect by 50% within 95% condidence limits, were determined by the method of Litchfield and Wilcoxon.

The results of these experiments are set out in Table I where R, $R_1$ and $R_2$ refer to the proceeding general formula for the compounds of the present invention. In the column under $R_2$ CBM stands for cyclobutylmethyl, CPM for cyclopropylmethyl, THF for tetrahydrofurfuryl and DMA for dimethylallyl. For purposes of this table, IA is intended to mean "inactive".

TABLE I

SUMMARY OF BIOLOGICAL DATA IN:
TEST A-ACETIC ACID MOUSE WRITHING TEST ($ED_{50}$)
TEST B-NARCOTIC ANTAGONIST ACTIVITY ($AD_{50}$)

| Compound | Example | R | $R_1$ | $R_2$ | $ED_{50}$ mg/kg | $AD_{50}$ mg/kg |
|---|---|---|---|---|---|---|
| TR-5296 | VI | $CH_3$ | H | CBM | 0.77 | IA at 10 |
| TR-5305 | VII | $CH_3$ | H | CPM | 0.98 | 1.60 |
| TR-5306 | IX | H | H | CBM | 0.007 | IA at 10 |
| TR-5325 | X | H | H | CPM | 0.45 | 0.35 |
| TR-5340 | XI | H | H | THF | 0.03 | IA at 10 |
| TR-5326 | VIII | $CH_3$ | H | THF | 0.16 | IA at 10 |
| TR-5284 | XXVII | H | $\alpha CH_3$ | CPM | IA at 10 | <3.0 |
| TR-5219 | XXVIII | $CH_3$ | $\alpha CH_3$ | CBM | 15.1 | IA at 10 |
| TR-5249 | XXIX | H | $\alpha CH_3$ | CBM | 0.14 | 3.0 |
| TR-5285* | XXX | H | $\alpha CH_3$ | CPM | >10 | >10 |
| TR-5310 | XXIV | H | $\alpha CH_3$ | DMA | 0.18 | IA at 10 |
| TR-5327 | XXV | $CH_3$ | $\alpha CH_3$ | THF | 1.85 | IA at 10 |
| TR-5209 | XXXIV | $CH_3$ | $\beta CH_3$ | CPM | IA at 13 | 0.45 |
| TR-5210 | XXXVI | H | $\beta CH_3$ | CPM | 30 | 0.004 |
| TR-5250* | XXXVIII | H | $\beta CH_3$ | CPM | IA at 10 | 0.32 |
| TR-5211 | XXXV | $CH_3$ | $\beta CH_3$ | CBM | IA at 10 | 0.41 |
| TR-5212 | XXXVII | H | $\beta CH_3$ | CBM | IA at 10 | 0.18 |
| TR-5400** | VII | $CH_3$ | H | CPM | 0.89 | 0.64 |

*OH at the 6-postion.
**free base of TR-5305

From Table I it can be determined that certain of the compounds tested are powerful analgesics, others are narcotic antagonists and some possess agonist/antagonist activity. Due to their low $ED_{50}$ values and high $AD_{50}$ values TR-5296, TR-5306, TR-5340, TR-5326, TR-5310 and TR-5327 can be considered pure analgesics. Those compounds which can be considered as pure narcotic antagonists due to their low $AD_{50}$ values and high $ED_{50}$ values are TR-5284, TR-5209, TR-5210, TR-5250, TR-5211, and TR-5212. Those compounds which possess mixed analgesic (agonist) and narcotic antagonist activity are TR-5305, TR-5325 and TR-5249. It can be determined that TR-5219 is not a narcotic antagonist and only a weak analgesic with $ED_{50}$ value of 15.1. However, TR-5249 which differs from TR-5219 solely by the displacement of the 3-methyl group with a hydrogen atom is active both as an analgesic and a narcotic antagonist. It is also noteworthy that TR-5285 is not active as an analgesic or a narcotic antagonist whereas TR-5284 which differs form TR-5285 by the presence of an oxo rather than hydroxyl at the 6-position is a narcotic antagonist. Another compound with a hydroxyl group rather than a double bond oxygen at the 6-position, i.e., TR-5250 shows some activity as a narcotic antagonist but is less active by nearly 2 orders of magnitude than TR-5210 which differs from it by the substitution of the hydroxyl with oxygen at the 6-position.

Those compounds which possess mixed agonist/antagonist activity, i.e., TR-5305, TR-5325, and TR-5249 are of special interest. Also of interest is TR-5210 which is a pure narcotic antagonist having an $AD_{50}$ of 0.004 which is 10 times as potent as naloxone, a well known narcotic antagonist.

The compounds of the present invention form pharmacologically active addition salts with organic and inorganic acids. Typical acid addition salts are the tartrate, hydrobromide, hydrochloride and maleate. The hydrochloride is preferred.

Those compounds which are pure analgesics are useful for relieving moderate to severe pain in an individual for whom such therapy is indicated whereas those compounds which have been found to be narcotic antagonists are useful for treating drug dependence in an individual for whom such theapy is indicated. Those compounds which are mixed analgesics/narcotic antagonists are useful for treating pain without the liability of drug dependence.

The term "individual" means a human being or an experimental animal that is a model for a human being. The dose to be administered to achieve the desired result, i.e., the effective dose, may vary from individual to individual but is readily determined by one skilled in the art without undue experimentation.

The compounds of the present invention may be administered by known, conventional methods of therapeutic administration such as intravenous, parenteral, buccal, rectal or oral. Dose forms for the administration of these compounds can be prepared by methods recognized in the pharmaceutical sciences.

What is claimed is:

1. 14-methoxy substituted 3-hydroxy or 3-methoxy-6-one morphinans characterized by the formula:

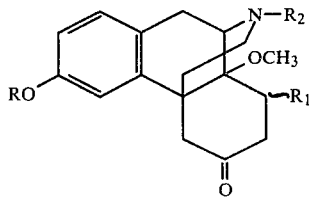

where R is H or methyl; $R_1$ is H, $\alpha$-methyl or $\beta$-methyl, and $R_2$ is cyclobutylmethyl, cyclopropylmethyl, tetrahydrofurfuryl or dimethylallyl, provided that when $R_2$ is dimethylallyl, $R_1$ is methyl.

2. The morphinans of claim 1 in the form of their pharmacologically acceptable, non-toxic acid addition salts.

3. A compound as defined by claim 1 wherein R is $C_3$, $R_1$ is H and $R_2$ is cyclobutylmethyl.

4. The hydrochloric acid addition salt of the compound defined by claim 3.

5. A compound as defined by claim 1 wherein R is $CH_3$, $R_1$ is H and $R_2$ is cyclopropylmethyl.

6. The hydrochloric acid addition salt of the compound defined by claim 5.

7. A compound as defined by claim 1 wherein R is H, $R_1$ is H and $R_2$ is cyclobutylmethyl.

8. The hydrochloric acid addition salt of the compound defined by claim 7.

9. A compound as defined by claim 1 wherein R is H, $R_1$ is H and $R_2$ is cyclopropylmethyl.

10. The hydrochloric acid addition salt of the compound defined by claim 9.

11. A compound as defined by claim 1 wherein R is H, $R_1$ is $\alpha$-methyl and $R_2$ is cyclopropylmethyl.

12. The hydrochloric acid addition salt of the compound defined by claim 11.

13. A compound as defined by claim 1 wherein R is H, $R_1$ is $\alpha$-methyl and $R_2$ is cyclobutylmethyl.

14. The hydrochloric acid addition salt of the compound defined by claim 13.

15. A compound as defined by claim 1 wherein R is H, $R_1$ is H and $R_2$ is tetrahydrofurfuryl.

16. The hydrochloric acid addition salt of the compound defined by claim 15.

17. A compound as defined by claim 1 wherein R is $CH_3$, $R_1$ is H and $R_2$ is tetrahydrofurfuryl.

18. The hydrochloric acid addition salt of the compound defined by claim 17.

19. A compound as defined by claim 1 wherein R is H, $R_1$ is $\alpha$-$CH_3$ and $R_2$ is dimethylallyl.

20. The hydrochloric acid addition salt of the compound defined by claim 19.

21. A compound as defined by claim 1 wherein R is $CH_3$, $R_1$ is $\alpha$-methyl and $R_2$ is tetrahydrofurfuryl.

22. The hydrochloric acid addition salt of the compound defined by claim 21.

23. A compound as defined by claim 1 wherein R is $CH_3$, $R_1$ is $\beta$-methyl and $R_2$ is cyclopropylmethyl.

24. The hydrochloric acid addition salt of the compound defined by claim 23.

25. A compound as defined by claim 1 wherein R is $CH_3$, $R_1$ is $\beta$-$CH_3$ and $R_2$ is cyclobutylmethyl.

26. The hydrochloric acid addition salt of the compound defined by claim 25.

27. A compound as defined by claim 1 wherein R is H, $R_1$ is $\beta$-$CH_3$ and $R_2$ is cyclobutylmethyl.

28. The hydrochloric acid addition salt of the compound defined by claim 27.

29. A compound as defined by claim 1 wherein R is H, $R_1$ is $\beta$-$CH_3$ and $R_2$ is cyclopropylmethyl.

30. The hydrochloric acid addition salt of the compound defined by claim 29.

31. As a composition of matter 17-cyclopropylmethyl-14-methoxy-8$\beta$-methyl-morphinan-3,6-diol hydrochloride.

32. A therapeutic method for treating pain in an individual for whom such therapy is indicated, which method comprises administering to the individual an effective analgesic amount of a compound selected from the group of 17-cyclobutylmethyl-3,14-dimethoxymorphinan-6-one, 17-cyclobutylmethyl-3-hydroxy-14-methoxymorphinan-6-one, 17-tetrahydrofurfuryl-3-hydroxy-14-methoxymorphinan-6-one, 17-tetrahydrofurfuryl-3,14-dimethoxymorphinan-6-one, 17-dimethylallyl-3-hydroxy-14-methoxy-8$\alpha$-methylmorphinan-6-one, 17-tetrahydrofurfuryl-3,14-dimethoxy-8$\alpha$-methylmorphinan-6-one or a pharmacological acceptable, non-toxic acid addition salt thereof.

33. The method of claim 32 wherein the compound is administered is in the form of its hydrochloric acid addition salt.

34. A therapeutic method for treating drug dependence in an individual for whom such therapy is indicated, which method comprises administering to the individual an effective narcotic antagonist amount of a compound selected from the group of 17-cyclopropylmethyl-3,14-dimethoxy-8$\beta$-methylmophinan-6-one; 17-cyclopropylmethyl-3-hydroxy-14-methoxy-8$\beta$-methylmorphinan-6-one; 17-cyclobutylmethyl-3,14-dimethoxy-8$\beta$-methylmorphinan-6-one; 17-cyclobutylmethyl-3-hydroxy-14-methoxy-8$\beta$-methylmorphinan-6-one; 17-cyclopropylmethyl-3-hydroxy-14-methoxy-8$\alpha$-methylmorphinan-6-one; 17-cyclopropylmethyl-14-methoxy-8$\beta$-methylmorphinan-3,6-diol or a pharmacologically acceptable, non-toxic acid addition salt thereof.

35. The method of claim 34 wherein the compound is administered in the form of its hydrochloric acid addition salt.

36. The method of claim 34 wherein the compound is 17-cyclopropylmethyl-3-hydroxy-14-methoxy-8$\beta$-methylmorphinan-6-one.

37. The method of claim 36 wherein the compound is administered in the form of its hydrochloric acid addition salt.

38. A therapeutic method for treating pain without liability of drug dependence in an individual for whom such therapy is indicated which method comprises administering to the individual an effective analgesic amount of a compound selected from the group of 17-cyclopropylmethyl-3,14-dimethoxymorphinan-6-one, 17-cyclopropylmethyl-3-hydroxy-14-methoxymorphinan-6-one, 17-cyclobutylmethyl-3-hydroxy-14-methoxy-8α-methylmorphinan-6-one or a pharmacologically acceptable, non-toxic acid addition salt thereof.

39. The method of claim 38 wherein the compound is administered in the form of its hydrochloric acid addition salt.

40. The method of claim 38 wherein the compound administered is 17-cyclopropylmethyl-3,14-dimethoxymorphinan-6-one.

41. The method of claim 40 wherein the compound is administered in the form of its hydrochloric acid addition salt.

42. The method of claim 38 wherein the compound administered is 17-cyclopropylmethyl-3-hydroxy-14-methoxymorphinan-6-one.

43. The method of claim 42 wherein the compound i is administered in the form of its hydrochloric acid addition salt.

44. The method of claim 38 wherein the compound administered is 17-cyclobutylmethyl-3-hydroxy-14-methoxy-8α-methylmorphinan-6-one.

45. The method of claim 44 wherein the compound is administered in the form of its hydrochloric acid addition salt.

46. The morphinans of claim 2 in the form of their tartrate salts.

* * * * *